US009308336B2

(12) United States Patent
Newton (10) Patent No.: US 9,308,336 B2
(45) Date of Patent: Apr. 12, 2016

(54) REFILL DIVERTER FOR ELECTRONIC CIGARETTE

(71) Applicant: Kyle D. Newton, Colleyville, TX (US)

(72) Inventor: Kyle D. Newton, Colleyville, TX (US)

(*) Notice: Subject to any disclaimer, the term of this patent is extended or adjusted under 35 U.S.C. 154(b) by 842 days.

(21) Appl. No.: 13/622,474

(22) Filed: Sep. 19, 2012

(65) Prior Publication Data

US 2014/0076310 A1 Mar. 20, 2014

(51) Int. Cl.
*A61M 15/06* (2006.01)
*A24F 47/00* (2006.01)
*A61M 15/00* (2006.01)
*A61M 11/04* (2006.01)

(52) U.S. Cl.
CPC .............. *A61M 15/06* (2013.01); *A24F 47/002* (2013.01); *A24F 47/004* (2013.01); *A24F 47/008* (2013.01); *A61M 11/042* (2014.02); *A61M 15/0091* (2013.01); *A61M 2205/8206* (2013.01); *A61M 2209/045* (2013.01)

(58) Field of Classification Search
CPC . A61M 15/06; A61M 15/00; A61M 15/0021; A61M 15/0085; A61M 15/0086; A61M 15/0091; A61M 11/00; A61M 11/041; A61M 11/04; A61M 11/08; A24F 47/002; A24F 47/008; A24F 47/004; A24F 47/00; A24F 13/02; A24F 13/06
USPC ............. 128/202.21; 137/329, 328, 270, 273, 137/194
See application file for complete search history.

(56) References Cited

U.S. PATENT DOCUMENTS

| 7,726,320 | B2 | 6/2010 | Robinson et al. | |
|---|---|---|---|---|
| 2005/0016550 | A1 | 1/2005 | Katase | |
| 2006/0196518 | A1 | 9/2006 | Hon | |
| 2007/0267031 | A1 | 11/2007 | Hon | |
| 2009/0095311 | A1 | 4/2009 | Han | |
| 2010/0031967 | A1 | 2/2010 | Inagaki | |
| 2013/0167853 | A1* | 7/2013 | Liu | 131/329 |
| 2013/0192618 | A1* | 8/2013 | Li et al. | 131/329 |
| 2013/0255675 | A1* | 10/2013 | Liu | 128/202.21 |

* cited by examiner

*Primary Examiner* — Justine Yu
*Assistant Examiner* — Colin W Stuart
(74) *Attorney, Agent, or Firm* — Dan Brown Law Office; Daniel R. Brown (57) ABSTRACT

A refillable atomizing assembly with a liquid reservoir for an electronic cigarette. The assembly includes a housing and a mouthpiece that is removably engaged to the housing. A liquid reservoir is disposed within the housing, and separated from the aerosol outlet by an outlet chamber. The liquid reservoir is refillable by removing the mouthpiece and dispensing the liquid into the outlet chamber. An atomizing chamber is adjacent to the reservoir and opposite of the outlet chamber. An aerosol conduit connects the atomizing chamber to the outlet chamber. An isolation member is disposed within the outlet chamber. A liquid passage through the isolation member allows the liquid placed into the outlet chamber to flow into the reservoir. A shield portion of the isolation member is located about the aerosol conduit to prevent liquid from entering. An aerosol vent through the shield portion enables the flow of the aerosol therethrough.

26 Claims, 5 Drawing Sheets

REFILL DIVERTER FOR ELECTRONIC CIGARETTE

BACKGROUND OF THE INVENTION

1. Field of the Invention

The present invention relates to electronic cigarettes. More specifically, the present invention relates to an electronic cigarette that is periodically refilled with a smoking liquid.

2. Description of the Related Art

Electronic cigarettes have become increasingly popular in recent times. Electronic cigarettes emulate a tobacco cigarettes, but without the combustion of tobacco during use. Rather than burning tobacco, a "smoking" liquid is atomized within the electronic cigarette, which emulates the smoke produced in a tobacco cigarette. The liquid may contain flavoring agents such as tobacco flavor, menthol, and others, to enhance the "smoking" experience of the electronic cigarette. Nicotine is added to the atomization liquid in certain electronic cigarettes. A reserve of liquid is stored within the cigarette housing in a porous material, which is placed into contact with an atomizing assembly such that the liquid can be gradually transferred to the atomizing assembly during consumption. Some electronic cigarettes are built as a disposable unit such that the cigarette is discarded once the reserve of smoking liquid is consumed. In other designs, a replaceable cartridge containing an atomizer assembly and a liquid soaked porous material is provided to enable consumers to replenish the supply of liquid as it is depleted during use by replacing the cartridge. However, it should be noted that the structural and electrical components in electronic cigarettes and atomizer cartridges are durable and far outlast the period of consumption of the typical quantity of liquid provided in such a porous reservoir.

In addition to replacing and discarding the liquid reservoir and atomizer cartridge, it is also possible for the end user to refill the liquid reservoir by adding more smoking liquid to the reservoir. However, since this is a consumer product, and since the assembly is relatively small and provides several operational functions, it is challenging to produce a cost effective structure that satisfies the design goal of an easily refillable cartridge that is also an effective and satisfying electronic cigarette. For example, the refill access opening must be simple and easy to open, and provide a tight seal when it is closed. It is also important to maintain the sealed relationship between the electrical interface, the liquid storage function, and the atomization and aerosol routing functions of the cartridge. This is particularly challenging when the liquid refill opening is located at or adjacent to either the electrical interface end or the mouthpiece end of the cartridge. Thus is can be appreciated that there is a need in the art for a refillable electronic cigarette cartridge assembly that addresses these problems in the prior art.

SUMMARY OF THE INVENTION

The need in the art is addressed by the apparatus of the present invention. The present disclosure teaches a refillable atomizing assembly with a liquid reservoir for an electronic cigarette. The assembly includes a housing and a mouthpiece with an aerosol outlet formed therethrough, and that is removably engaged with the housing. A liquid reservoir is disposed within the housing, and separated from the aerosol outlet by an outlet chamber. The liquid reservoir is refillable by removing the mouthpiece and dispensing the liquid into the outlet chamber. An atomizing chamber, with an atomizer inside, is adjacent to the reservoir and opposite of the outlet chamber. An aerosol conduit, which passes through the liquid reservoir from the atomizing chamber to the outlet chamber, communicates an aerosol of the liquid generated by the atomizer in response to a negative pressure induced at the mouthpiece. An isolation member is disposed within the outlet chamber and arranged to substantially seal the liquid reservoir from the outlet chamber. A liquid passage through the isolation member allows the liquid placed into the outlet chamber to flow into the reservoir. A shield portion of the isolation member is located about the aerosol conduit to prevent liquid from entering. An aerosol vent through a periphery of the shield portion enables the flow of the aerosol therethrough. The aerosol vent is further oriented to prevent liquid from entering the aerosol passage.

In a specific embodiment of the foregoing apparatus, the housing is cylindrical and provides the outer enclosure of the liquid reservoir and the outlet chamber, and the mouthpiece is formed from a polymeric material that engages the housing. In another specific embodiment, the liquid reservoir has an end open to the outlet chamber, which enables the liquid to enter. In another specific embodiment, the liquid reservoir is filled with an absorbent material to contain the liquid. In another specific embodiment, the aerosol conduit is a tube, which defines the inner wall of the liquid reservoir.

In a specific embodiment of the foregoing apparatus, the isolation member is formed from a resilient polymeric material. In another specific embodiment, the isolation member engages the inside surface of the housing.

In a specific embodiment of the foregoing apparatus, the liquid passage is aligned along an axis substantially parallel with the aerosol conduit. In another specific embodiment, the liquid flows thorough the liquid passage by gravity when the aerosol conduit is oriented in a substantially vertical direction. In another specific embodiment, the aerosol conduit includes an extension that extends further into the outlet chamber than the liquid reservoir, and the shield portion accommodates the extension. In another specific embodiment, the shield portion is configured as a cap over an end of the aerosol conduit.

In a specific embodiment of the foregoing apparatus, the aerosol vent is aligned along an axis substantially perpendicular to the aerosol conduit. In another specific embodiment, the aerosol vent is disposed radially away from an open end of the aerosol conduit.

The present disclosure teaches a refillable atomizing assembly with a liquid reservoir for an electronic cigarette. The assembly includes a housing and a mouthpiece with an aerosol outlet formed therethrough, and that is removably engaged with the housing. A liquid reservoir is disposed within the housing, and separated from the aerosol outlet by an outlet chamber. The liquid reservoir is refillable by removing the mouthpiece and dispensing the liquid into the outlet chamber. An atomizing chamber, with an atomizer inside, is adjacent to the reservoir and opposite of the outlet chamber. An aerosol conduit, which passes through the liquid reservoir from the atomizing chamber to the outlet chamber, communicates an aerosol of the liquid generated by the atomizer in response to a negative pressure induced at the mouthpiece. An isolation member is disposed within the outlet chamber and is arranged to substantially seal the liquid reservoir from the outlet chamber. A shield portion of the isolation member is located about the aerosol conduit to prevent liquid from entering there into. A passage through the isolation member allows the liquid within the outlet chamber to flow into the reservoir. It also enables the flow of the aerosol therethrough, and is further oriented to prevent liquid from entering the aerosol passage.

In a specific embodiment of the foregoing apparatus, the housing is cylindrical and provides the outer enclosure of the liquid reservoir and the outlet chamber, and the mouthpiece is formed from a polymeric material that engages the housing. In another specific embodiment, the liquid reservoir has an end open to the outlet chamber, which enables the liquid to enter. In another specific embodiment, the liquid reservoir is filled with an absorbent material to contain the liquid.

In a specific embodiment of the foregoing apparatus, the aerosol conduit is a tube that defines the inner wall of the liquid reservoir. In another specific embodiment, the isolation member is formed from a resilient polymeric material. In another specific embodiment, the isolation member engages an inside surface of the housing.

In a specific embodiment of the foregoing apparatus, the liquid passage is aligned along an axis substantially parallel with the aerosol conduit. In another specific embodiment, the liquid flows thorough the passage by gravity when the aerosol conduit is oriented in a substantially vertical direction. In another specific embodiment, the aerosol conduit includes an extension that extends further into the outlet chamber than the liquid reservoir, and the shield portion accommodates the extension.

In a specific embodiment of the foregoing apparatus, the shield portion is configured as a cap over an end of the aerosol conduit. In another specific embodiment, the passage includes a vent portion, which is aligned along an axis substantially perpendicular to the aerosol conduit. In another specific embodiment, the passage is disposed radially away from an open end of the aerosol conduit.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof and additional fields in which the present invention would be of significant utility.

In considering the detailed embodiments of the present invention, it will be observed that the present invention resides primarily in combinations of steps to accomplish various methods or components to form various apparatus and systems. Accordingly, the apparatus and system components and method steps have been represented where appropriate by conventional symbols in the drawings, showing only those specific details that are pertinent to understanding the present invention so as not to obscure the disclosure with details that will be readily apparent to those of ordinary skill in the art having the benefit of the disclosures contained herein.

In this disclosure, relational terms such as first and second, top and bottom, upper and lower, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

The present disclosure advances the art of electronic cigarettes by teaching an electronic cigarette with an assembly including an atomizer and a refillable liquid reservoir, which can be easily refilled through the mouthpiece end without inadvertently flooding the atomizer chamber, yet still provides efficient liquid flow management and atomization. This is accomplished by utilizing a refill flow diverter that routes the liquid to a liquid reservoir during the refill operation, while also providing a pathway for atomized aerosol to exit the mouthpiece during use. Some of the components and processes discussed in this disclosure have been previously disclosed by the inventor hereof of earlier filed patent applications. The reader may benefit from a review of these disclosures, where are hereby incorporated herein by the following references. The inventor of the present disclosure hereby incorporates the entire disclosure of previous filed U.S. patent application Ser. No. 12/882,293, filed on Sep. 15, 2010 for Electronic Cigarette with Function Illuminator. The inventor of the present disclosure hereby incorporates the entire disclosure in previous filed U.S. patent application Ser. No. 13/157,024, filed on Jun. 28, 2011 for Electronic Cigarette with Liquid Reservoir.

Figure 1:
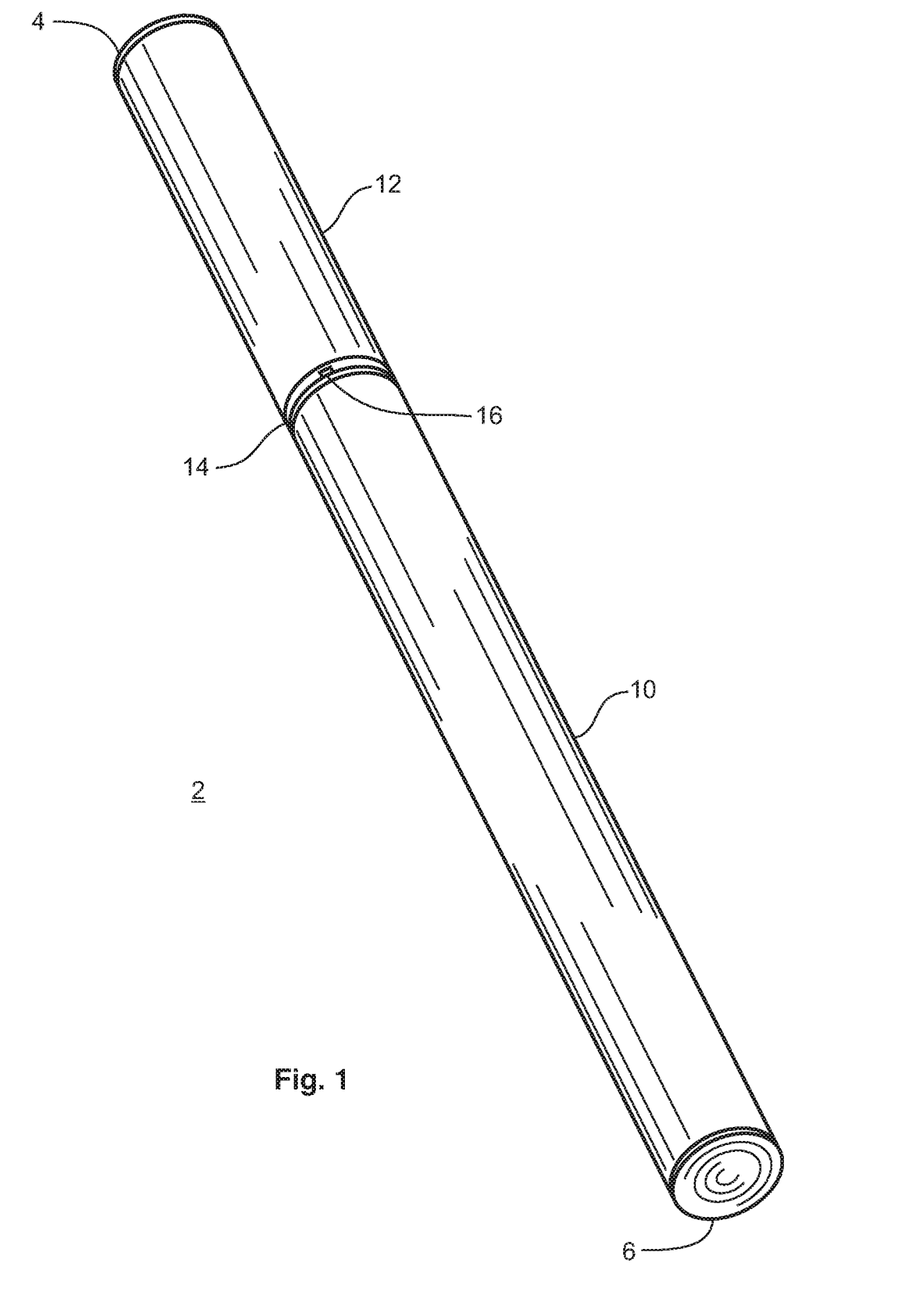
FIG. 1 is a perspective view drawing of an electronic cigarette according to an illustrative embodiment of the present invention.

Reference is directed to FIG. 1, which is a perspective view drawing of an electronic cigarette 2 according to an illustrative embodiment of the present invention. The electronic cigarette 2 comprises a housing having a first elongated portion 10 and an atomizer and liquid reservoir assembly 12, which is also referred to as a "cartridge assembly" or by the term "cartomizer". "Cartomizer is a contraction of "cartridge" and "atomizer". The cartridge assembly 12 comprises a mouthpiece end 4, which has an aerosol outlet (not shown) for drawing air through the cartridge assembly 12. The first elongated portion 10 and the cartridge assembly 12 are removable joined together with a mechanical coupler 14. One or more air inlet vents 16 are provided about the coupler 14 for allowing airflow into the cartridge assembly 12 when the user draws air through the mouthpiece end 4. The first elongated portion 10 comprises a tip end 6, which in the illustrative embodiment, is fabricated from a translucent material enabling the transmission of light therethrough. Within the cartridge assembly 12 is disposed a liquid reservoir (not shown).

Figures 2A, 2B, 2C, 3, 4:
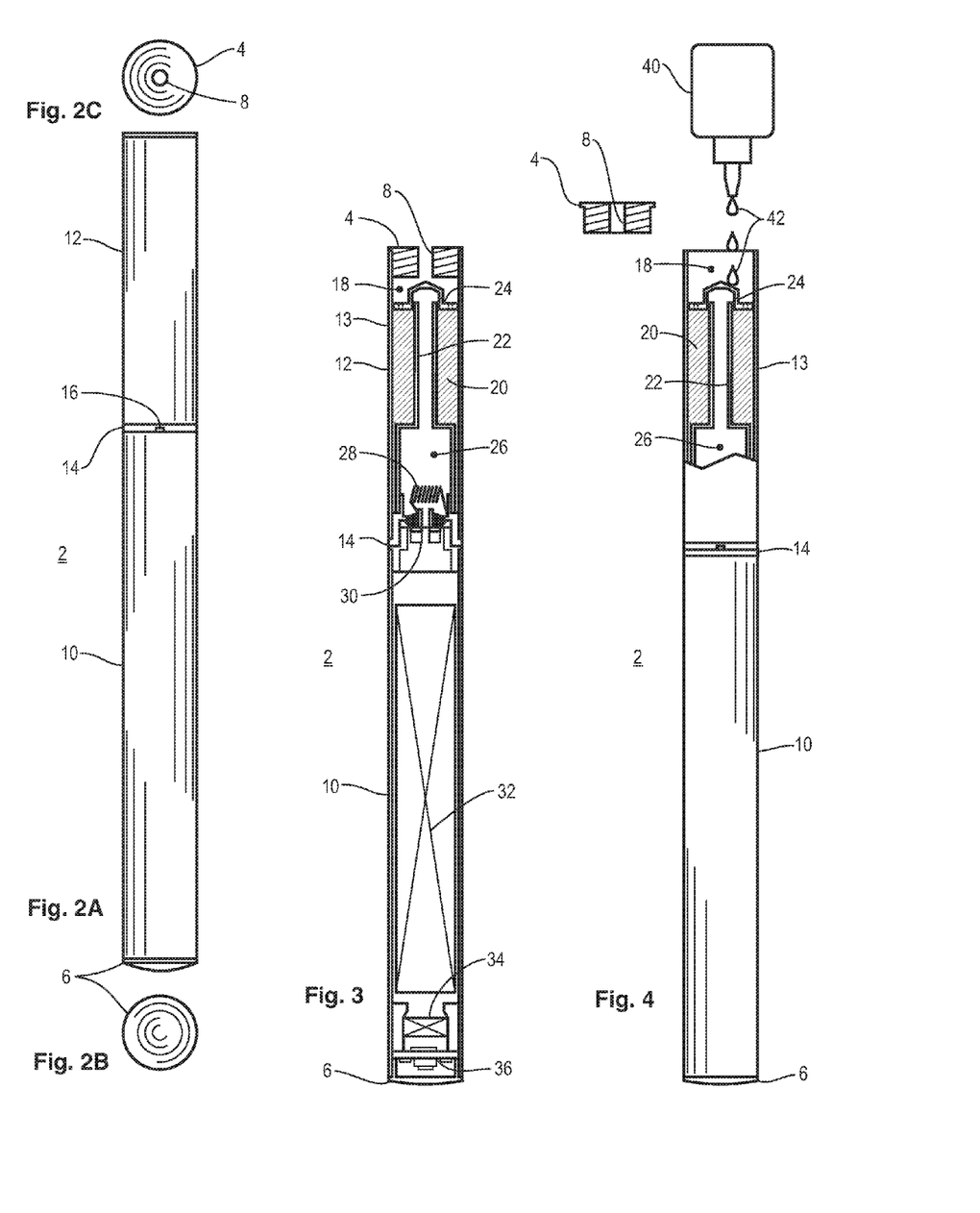
FIGS. 2a, 2b, and 2c are a tip end view, a side view, and mouthpiece end view, respectively, drawings of an electronic cigarette according to an illustrative embodiment of the present invention.
FIG. 3 is a cross section view drawing of an electronic cigarette according to an illustrative embodiment of the present invention.
FIG. 4 is a partial cross section view drawing of an electronic cigarette being refilled according to an illustrative embodiment of the present invention.

Now, considering FIGS. 2A, 2B, and 2C, these are a side view, a tip end view, and mouthpiece end view, respectively, drawing of an electronic cigarette 2 according to an illustrative embodiment of the present invention. Note that the first elongated portion 10 and the cartomizer 12 combine at coupler 14 to present a complete electronic cigarette 2 that closely resembles a tobacco cigarette. The cartridge assembly 12 may fabricated with a finished material resembling the filter of a tobacco cigarette, and the first elongated portion 10 is fabricated to resemble the tobacco roll of a tobacco cigarette. The mouthpiece end 4 includes an aerosol outlet opening 8, for drawing air and aerosol out of the cartridge assembly 12. Air is inlet to the electronic cigarette 2 at the vent openings 16 located at the coupler 14. The air inlet openings 16 can be located elsewhere on the electronic cigarette 2, and is a matter of design choice. In the illustrative embodiment, the tip end 6 is a translucent gray material resembling an ash.

Reference is directed to FIG. 3, which is a side section view drawing of an electronic cigarette according to an illustrative embodiment of the present invention. The mouthpiece end 4 is a resilient mouthpiece that engages the interior of the cartridge housing 13 and provides the aerosol outlet 8, which is a passage formed therethrough. Within the cartridge assembly 12 is an atomizing chamber 26 that has an open aerosol conduit 22 extending to an outlet chamber 18. The annular space formed between the interior of the cartridge housing 13 and the aerosol conduit 22 defines the liquid reservoir 20. In the illustrative embodiment, the liquid reservoir 20 includes a porous material for holding the smoking liquid. The lower end of the liquid reservoir 20 is adjacent to the atomizing chamber 26, and provides a flow of the smoking liquid to the atomizer 28 by capillary flow. Within the outlet chamber 18 is disposed a flow diverter 24, also referred to as an isolation member 24, which will be more fully described hereinafter.

In FIG. 3, the atomizer 28 is disposed within the atomizer chamber 26. In addition, the cartridge assembly 12 comprises the mechanical coupler 14 that engages the first elongated portion 10. Within the mechanical coupler 14, is an electrical coupler 30 that has an air inlet port formed therethrough, which is pneumatically coupled into the atomizing chamber 26. Thusly, the pathway for the flow of fresh air in and aerosol out includes air drawn through the mechanical coupler vents 16, through the air inlet port 31, to the atomizer 28 within the atomizing chamber 26, up the aerosol conduit 22, and so forth, as will be more fully discussed hereinafter.

In FIG. 3, the first elongated portion 10 of the housing has a threaded extension that engages the mechanical coupler 14. There is also a corresponding electrical connection such that the power supply portion 10 can deliver electric current to the atomizer 28 to facilitate generation of aerosol. Two conductors are provided, including the outer mechanical connection and the central pneumatic/electric connection 30. Suitable milling for air-flow channels is provided to facilitate solid mechanical, conductive electrical, and pneumatic connections. In the illustrative embodiment, power is derived from a storage battery 32. A pressure sensor 34 detects negative pressure within the housing 10 and energizes the atomizer. A draw circuit 36 provides the electrical operation functions. In addition, and amber LED is disposed to illuminate through the translucent tip 6 to emulate burning ash while the draw pressure sensor 34 detects negative pressure.

Reference is directed to FIG. 4, which is a partial cross section view drawing of an electronic cigarette 2 being refilled according to an illustrative embodiment of the present invention. The components identified in FIG. 4 correspond to those discussed in regards to FIG. 3. In FIG. 4, the mouthpiece 4 has been removed from the open end of the cartomizer housing 13, to facilitate the addition of drops 42 of smoking liquid dispensed from a suitable dispenser 40. The isolation member 24 disposed within the outlet chamber 18 prevents the drops 42 from entering the aerosol conduit 22 and flooding the atomizing chamber 26. Rather, the drops 42 are diverted to a liquid passage (discussed hereinafter) portion of the isolation member 24 that allows them to flow into the liquid reservoir 20. In addition, there are aerosol vents (discussed hereinafter) in the isolation member 24 that allow the aerosol to flow from the aerosol conduit 22 into the outlet chamber 18 when the user draws upon the mouthpiece 4.

Figure 5:
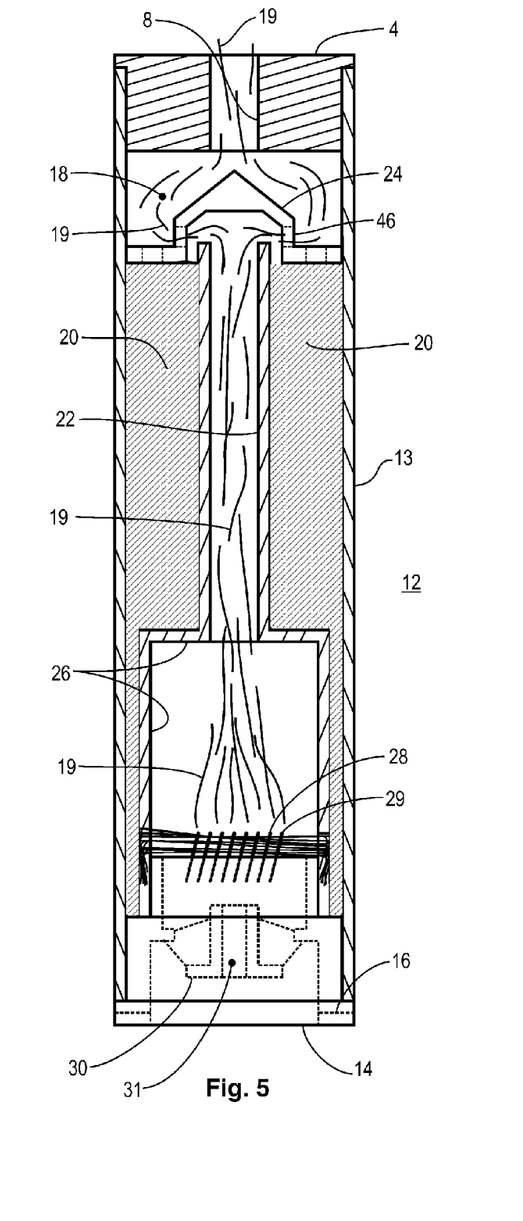
FIG. 5 is a detailed view drawing of a cartomizer for an electronic cigarette according to an illustrative embodiment of the present invention.

Reference is directed to FIG. 5, which is a detailed view drawing of a cartomizer 12 for an electronic cigarette according to an illustrative embodiment of the present invention. Further details are presented in this figure, and the reference numerals are consistent with those present in FIGS. 3 and 4. In FIG. 5, a metal cylindrical housing 13 forms the cartomizer 12, with a resilient mouthpiece 4 having an aerosol outlet 8 formed therethrough at the upper end. At the lower end of the housing 13 is the mechanical coupler 14 with inlet vents 16. The electrical coupler 30 and pneumatic passage 31 to the atomizing chamber 26 are illustrated. Within the atomizing chamber 26 is the atomizer 28, which is a resistive heating element wrapped about a bundle of fibers 29 that pass into the liquid reservoir 20 at its lowest end. This arrangement provides for the capillary flow of smoking liquid to the atomizer 28. At the upper end of the atomizing chamber is the aerosol conduit 22, which passes through the liquid reservoir 20 and enters the outlet chamber 18.

The liquid reservoir 22, in FIG. 5, is bound by the interior wall of the housing 13 and the exterior wall of the aerosol conduit 22. At the upper end of the liquid reservoir is open to the outlet chamber 18. Since the liquid reservoir is filled with a suitable porous material, smoking liquid that enters the liquid reservoir 20 is entrained into the porous material. The flow diverter, or isolation member, 24 directs the flow of liquid into the liquid reservoir 20 as well as the flow of aerosol out of the aerosol conduit 22. The flow of aerosol functions as follows. The motive force for air and aerosol flow through the cartomizer 12 is the suction applied to the mouthpiece 4, and the aerosol outlet 8 by the user. This action induces fresh airflow into the cartomizer 12 through the inlet vents 16. The air travels upward through the passage 31 formed in the electrical coupler 30 and into the atomization chamber 26. The suction also switches the atomizer 28 on to heat, which atomizes the smoking liquid into an aerosol 19. The aerosol 19 is drawn out of the atomizing chamber 26 and up the aerosol conduit 22. The aerosol 19 is further drawn through aerosol vents 46 formed in the isolation member 24, and into the outlet chamber 18. From there, the aerosol 19 passes out of the cartomizer 12 through the aerosol outlet 8 formed through the mouthpiece 4. Note that the aerosol conduit 22 extends further up than the liquid reservoir and that the aerosol vents 46 are arranged orthogonal to the general upward flow path. This arrangement resists the flow of liquid through the aerosol vents 46. In addition, if liquid would enter the vents 46, the vents 46 are disposed radially away from the outlet end of the aerosol conduit 22, so the liquid would travel downwardly into the liquid reservoir by either capillary flow or due to the adhesion of surface tension.

Figure 6A:
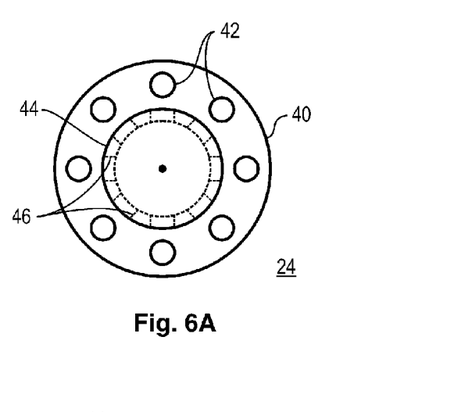
FIGS. 6A, 6B, and 6C are a top view, section view, and bottom view drawing, respectively, of a refill liquid flow diverter for an electronic cigarette according to an illustrative embodiment of the present invention.
Figure 6B:
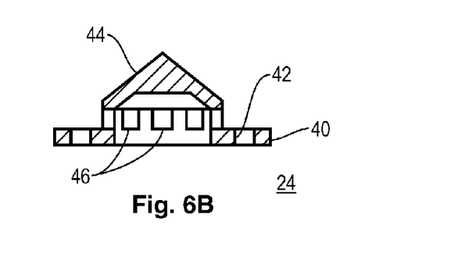
Figure 6C:
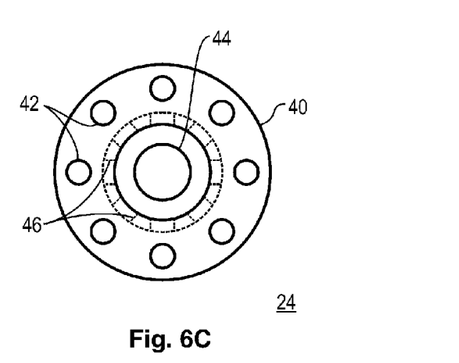

Reference is directed to FIGS. 6A, 6B, and 6C, which are a top view, section view, and bottom view drawing, respectively, of a refill liquid flow diverter 24 for an electronic cigarette according to an illustrative embodiment of the present invention. The refill liquid flow diverter can also be referred to as an isolation member 24. The body is formed as a planar member 40 that is generally configured in a shape consistent with the exterior wall of the liquid reservoir (not shown). In the illustrative embodiment, this is a disc, and, insertion of the planar member 40 into the outlet chamber (not shown) generally seals the liquid reservoir (not shown) from the outlet chamber. The isolation member 24 also includes a shield portion 44, which extends upwardly and is aligned and disposed above the end of the aerosol conduit (not shown). The upper end of the shield 44 may be conical in form so as to divert drops of liquid that impinge upon it to flow downwardly to the planar member 40. Other suitable configuration may be employed.

The sealing feature of the isolation member enables the control of the flow of liquids downwardly through it and aerosols upwardly through it using certain passages and vents. In particular, the planar member 40 has one or more liquid passages 42 that are formed through it. These liquid passages allow any drops of liquid that are placed thereupon to flow downwardly into the liquid reservoir (not shown). Since the liquid passages 42 are located directly above the liquid reservoir, there is no other place that such liquid can flow to. The isolation member 24 also includes one or more aerosol vents 46. The aerosol vents 46 are preferable aligned orthogonally to the liquid passages 42. The side wall of the shield portion 44 is a suitable location for the aerosol vents 46. Note that the aerosol vents 46 are disposed radially away from the center of the shield 44, such that any liquid that might pass through the aerosol vents 46 would not drain downwardly into the aerosol conduit (not shown). The isolation member may be made of any suitable material, and in the illustrative embodiment, a resilient polymeric material is used.

Figure 7A:
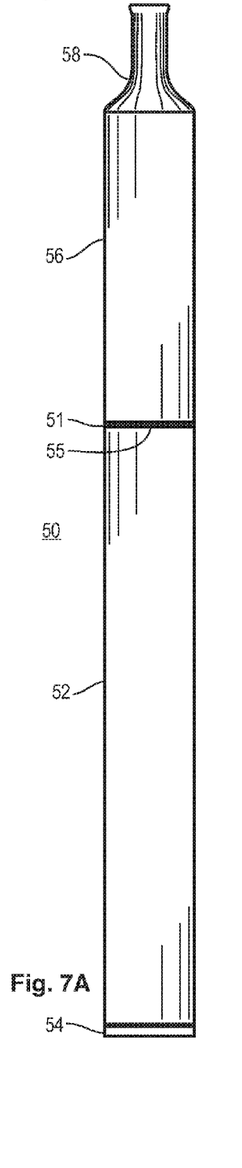
FIGS. 7A and 7B are a mouthpiece end view and a side view drawing, respectively, of an electronic cigarette according to an illustrative embodiment of the present invention.
Figure 7B:
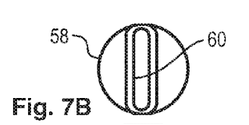

Reference is directed to FIGS. 7A and 7B, which are a mouthpiece end view and a side view drawing, respectively, of an electronic cigarette according to an illustrative embodiment of the present invention. The electronic cigarette 50 comprises a housing having a first elongated portion 52 and an atomizer and liquid reservoir assembly 56, also referred to as a "cartridge assembly" or "cartomizer". In this illustrative embodiment, the cartridge assembly 56 comprises a larger resilient mouthpiece end 58, which has an aerosol outlet 60 for drawing air through the cartridge assembly 56. This illustrative embodiment is similar to a tobacco cigar with an attached mouthpiece. The first elongated portion 52 and the cartridge assembly 56 are removable joined together with a mechanical coupler 51. One or more air inlet vents 55 are provided about the coupler 51 for allowing airflow into the cartridge assembly 56 when the user draws air through the mouthpiece end 58. The first elongated portion 52 comprises a tip end 54. Within the cartridge assembly 56 is disposed a liquid reservoir (not shown). Note that the first elongated portion 52 and the cartomizer 56 combine at coupler 51 to present a complete electronic cigarette 50 that closely resembles a tobacco cigar, and which provides a larger assembly for containing a larger liquid reservoir and a more powerful battery. The mouthpiece end 58 includes an aerosol outlet opening 60, for drawing air and aerosol out of the cartridge assembly 56.

Figure 8:
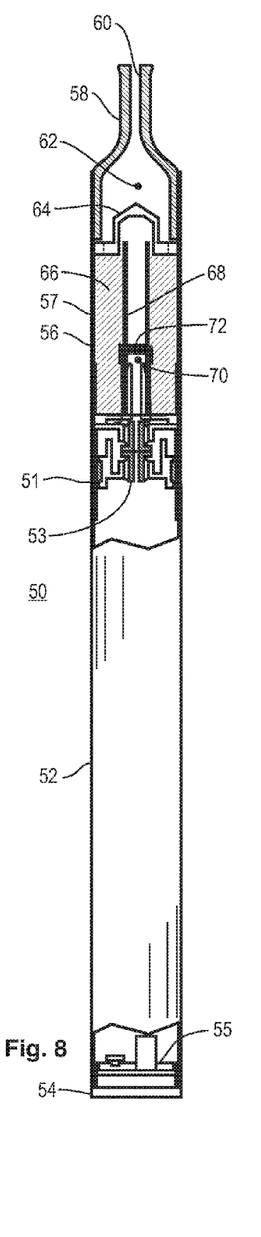
FIG. 8 is a cross section view drawing of an electronic cigarette according to an illustrative embodiment of the present invention.

Reference is directed to FIG. 8, which is a cross section view drawing of an electronic cigarette 50 according to an illustrative embodiment of the present invention. The mouthpiece end 58 is a resilient mouthpiece that engages the interior of the cartridge housing 57 and provides the aerosol outlet 60, which is a passage formed therethrough. Within the cartridge assembly 56 is an atomizing chamber 70 that has an open aerosol conduit 68 extending to an outlet chamber 62. The annular space formed between the interior of the cartridge housing 57 and the aerosol conduit 68 defines the liquid reservoir 66. In the illustrative embodiment, the liquid reservoir 66 includes a porous material for holding the smoking liquid. The lower end of the liquid reservoir 66 is adjacent to the atomizing chamber 70, and provides a flow of the smoking liquid to the atomizer 72 by capillary flow. Within the outlet chamber 62 is disposed a flow diverter 64, also referred to as an isolation member 64, which will be more fully described hereinafter. The atomizer 72 is disposed within the atomizer chamber 70. In addition, the cartridge assembly 56 comprises the mechanical coupler 51 that engages the first elongated portion 52. Within the mechanical coupler 51, is an electrical coupler 53 that has an air inlet port formed therethrough, which is pneumatically coupled into the atomizing chamber 70.

Thusly, in FIG. 8, the pathway for the flow of fresh air in and aerosol out includes air drawn through the mechanical coupler vents 55 (not shown), through the air inlet port 54, to the atomizer 72 within the atomizing chamber 70, up the aerosol conduit 68, and so forth, as will be more fully discussed hereinafter. The first elongated portion 52 of the housing has a threaded extension that engages the mechanical coupler 51. There is also a corresponding electrical connection such that the power supply portion (not shown) can deliver electric current to the atomizer 72 to facilitate generation of aerosol. Two conductors are provided, including the outer mechanical connection and the central pneumatic/electric connection 53. Suitable milling for air-flow channels is provided to facilitate solid mechanical, conductive electrical, and pneumatic connections. In the illustrative embodiment, power is derived from a storage battery (not shown).

Figure 9:
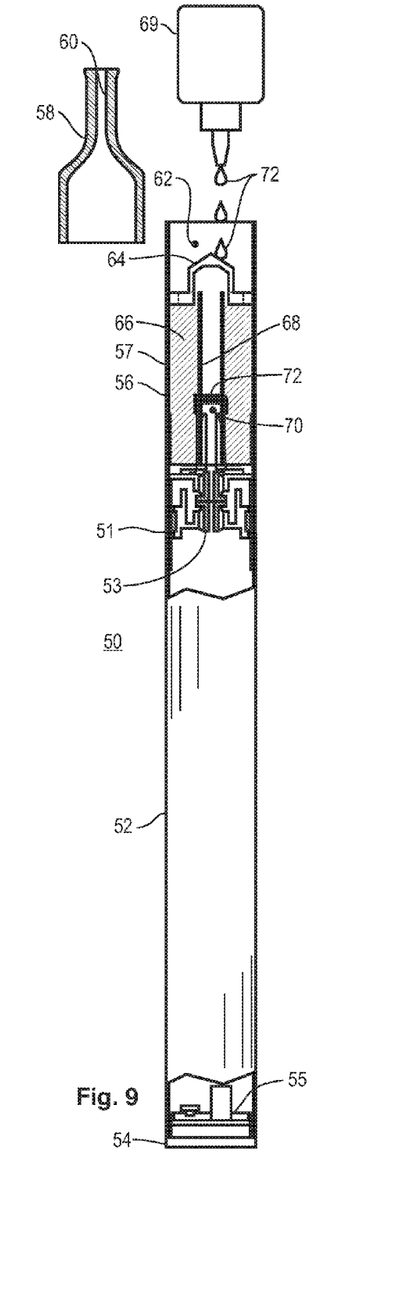
FIG. 9 is a partial cross section view drawing of an electronic cigarette being refilled according to an illustrative embodiment of the present invention.

Reference is directed to FIG. 9, which is a partial cross section view drawing of an electronic cigarette being refilled according to an illustrative embodiment of the present invention. The components identified in FIG. 9 correspond to those discussed in regards to FIG. 8. In FIG. 9, the mouthpiece 58 has been removed from the open end of the cartomizer housing 57, to facilitate the addition of drops 72 of smoking liquid dispensed from a suitable dispenser 69. The isolation member 64 disposed within the outlet chamber 62 prevents the drops 72 from entering the aerosol conduit 68 and flooding the atomizing chamber 70. Rather, the drops 72 are diverted to a liquid passage (discussed hereinafter) portion of the isolation member 64 that allows them to flow into the liquid reservoir 66. In addition, there are aerosol vents (discussed hereinafter) in the isolation member 64 that allow the aerosol to flow from the aerosol conduit 68 into the outlet chamber 62 when the user draws upon the mouthpiece 58.

Figure 10:
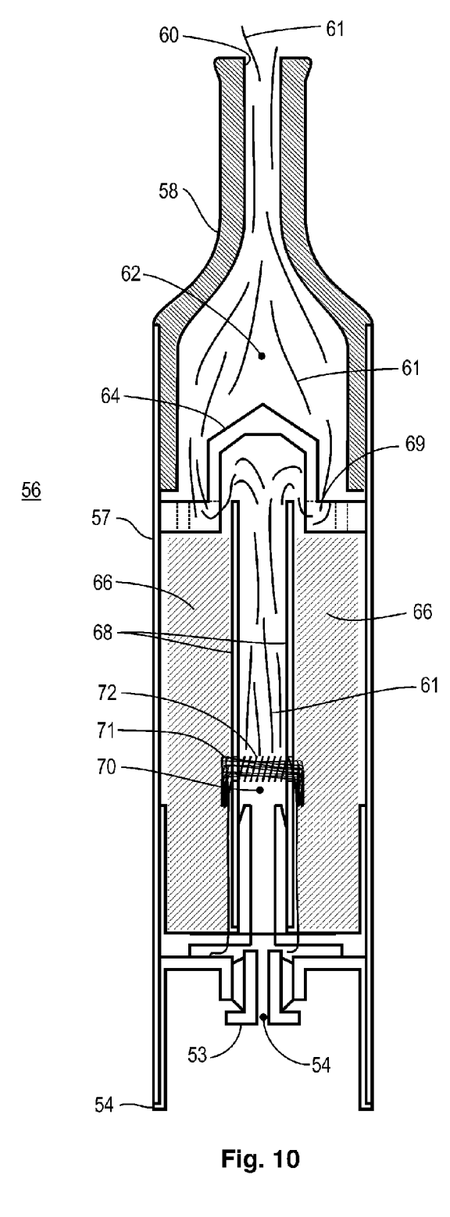
FIG. 10 is a detailed view drawing of a cartomizer for an electronic cigarette according to an illustrative embodiment of the present invention.

Reference is directed to FIG. 10, which is a detailed view drawing of a cartomizer for an electronic cigarette according to an illustrative embodiment of the present invention. Further details are presented in this figure, and the reference numerals are consistent with those present in FIGS. 8 and 9. In FIG. 10, a metal cylindrical housing 57 forms the cartomizer 56, with a resilient mouthpiece 58 having an aerosol outlet 60 formed therethrough at the upper end. At the lower end of the housing 57 is the mechanical coupler 54 with inlet vents (not shown). The electrical coupler 53 and pneumatic passage 54 to the atomizing chamber 70 are illustrated. Within the atomizing chamber 70 is the atomizer 72, which is a resistive heating element wrapped about a bundle of fibers 71 that pass into the liquid reservoir 66. This arrangement provides for the capillary flow of smoking liquid to the atomizer 72. At the upper end of the atomizing chamber is the aerosol conduit 68, which passes through the liquid reservoir 66 and enters the outlet chamber 62. The liquid reservoir 66 is bound by the interior wall of the housing 57 and the exterior wall of the aerosol conduit 68. At the upper end of the liquid reservoir 66 is open to the outlet chamber 62. Since the liquid reservoir is filled with a suitable porous material, smoking liquid that enters the liquid reservoir 66 is entrained into the porous material. The flow diverter, or isolation member, 64 directs the flow of liquid into the liquid reservoir 66 as well as the flow of aerosol out of the aerosol conduit 68.

The flow of aerosol in FIG. 10 functions as follows. The motive force for air and aerosol flow through the cartomizer 56 is the suction applied to the mouthpiece 58, and the aerosol outlet 60 by the user. This action induces fresh airflow into the cartomizer 56 through the inlet vents (not shown) along the coupler 54. The air travels upward through the passage 54 formed in the electrical coupler 53 and into the atomization chamber 70. The suction also switches the atomizer 70 on to heat, which atomizes the smoking liquid into an aerosol 61. The aerosol 61 is drawn out of the atomizing chamber 70 and up the aerosol conduit 68. The aerosol 61 is further drawn through aerosol vents 69 formed in the isolation member 64, and into the outlet chamber 62. From there, the aerosol 61 passes out of the cartomizer 56 through the aerosol outlet 60 formed through the mouthpiece 58. Note that the aerosol conduit 68 extends further up than the liquid reservoir 66 and that the aerosol vents 69 are arranged orthogonal to the general upward flow path. This arrangement resists the flow of liquid through the aerosol vents 69. In addition, if liquid would enter the vents 69, the vents 69 are disposed radially away from the outlet end of the aerosol conduit 68, so the liquid would travel downwardly into the liquid reservoir by either capillary flow or due to the adhesion of surface tension.

Figure 11A:
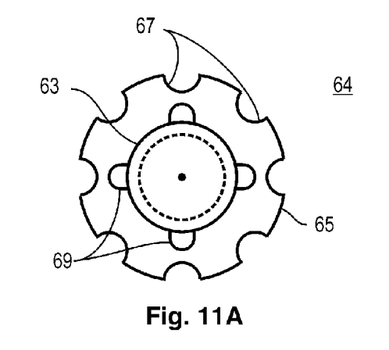
FIGS. 11A, 11B, and 11C are a top view, section view, and bottom view drawing, respectively, of a refill liquid flow diverter for an electronic cigarette according to an illustrative embodiment of the present invention.
Figure 11B:
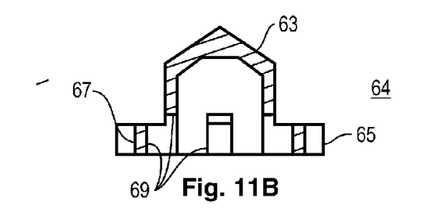
Figure 11C:
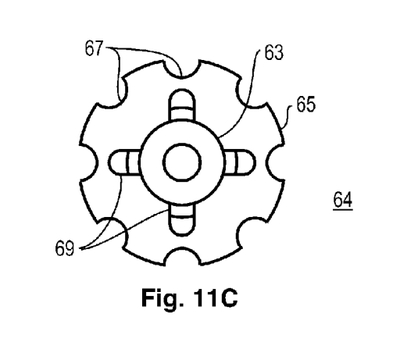

Reference is directed to FIGS. 11A, 11B, and 11C, which are a top view, section view, and bottom view drawing, respectively, of a refill liquid flow diverter 64 for an electronic cigarette according to an illustrative embodiment of the present invention. The refill liquid flow diverter 64 can also be referred to as an isolation member 64. The body is formed as a planar member 65 that is generally configured in a shape consistent with the exterior wall of the liquid reservoir (not shown). In the illustrative embodiment, this is a disc, and, insertion of the planar member 65 into the outlet chamber (not shown) generally seals the liquid reservoir (not shown) from the outlet chamber. The isolation member 64 also includes a shield portion 63, which extends upwardly and is aligned and disposed above the end of the aerosol conduit (not shown). The upper end of the shield 63 may be conical in form so as to divert drops of liquid that impinge upon it to flow downwardly to the planar member 65. Other suitable configuration may be employed.

The sealing feature of the isolation member enables the control of the flow of liquids downwardly through it and aerosols upwardly through it using certain passages and vents. In particular, the planar member 65 has one or more liquid passage recesses 67 that are formed on its exterior edge. These liquid passages allow any drops of liquid that are placed thereupon to flow downwardly into the liquid reservoir (not shown). Since the liquid passages 67 are located directly above the liquid reservoir, there is no other place that such liquid can flow to. The isolation member 64 also includes one or more aerosol vents 69. The aerosol vents 69 are disposed radially away from the center of the shield 63, such that any liquid that might pass through the aerosol vents 69 would not drain downwardly into the aerosol conduit (not shown). The isolation member 64 may be made of any suitable material, and in the illustrative embodiment, a resilient polymeric material is used. Note that in this illustrative embodiment, the aerosol vents 69 are disposed both vertically along the side wall of the shield portion 63, and also horizontally along the surface of the planar portion 65. This arrangement enables the aerosol vents 69 to also provide the requisite liquid passage function. For this reason, it is also acceptable to omit the liquid passages 67 from this isolation member 64 structure.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. An atomizing assembly with a liquid reservoir, which is refillable, for an electronic cigarette, comprising:
   a housing;
   a mouthpiece with an aerosol outlet formed therethrough, removably engaged with said housing;
   a liquid reservoir disposed within said housing, and separated from said aerosol outlet by an outlet chamber, said liquid reservoir refillable by removing said mouthpiece and dispensing liquid into said outlet chamber;
   an atomizing chamber, with an atomizer therein, adjacent to said liquid reservoir and opposite of said outlet chamber;
   an aerosol conduit, which passes through said liquid reservoir, from said atomizing chamber to said outlet chamber, and which communicates an aerosol of liquid generated by said atomizer in response to a negative pressure induced at said mouthpiece;
   an isolation member disposed within said outlet chamber and arranged to substantially seal said liquid reservoir from said outlet chamber;
   a liquid passage through said isolation member, which allows liquid within said outlet chamber to flow into said liquid reservoir;
   a shield portion of said isolation member located about said aerosol conduit to prevent liquid from entering there into, and
   an aerosol vent through a periphery of said shield portion, which enables flow of said aerosol therethrough, and further oriented to prevent liquid from entering said aerosol conduit.

2. The assembly of claim 1, and wherein:
   said housing is cylindrical and provides an outer enclosure of said liquid reservoir and said outlet chamber, and wherein
   said mouthpiece is formed from a polymeric material that engages said housing.

3. The assembly of claim 1, and wherein:
said liquid reservoir has an end open to said outlet chamber, thereby enabling liquid to enter.

4. The assembly of claim 3, and wherein:
said liquid reservoir is filled with an absorbent material to contain liquid.

5. The assembly of claim 1, and wherein:
said aerosol conduit is a tube, which defines an inner wall of said liquid reservoir.

6. The assembly of claim 1, and wherein:
said isolation member is formed from a resilient polymeric material.

7. The assembly of claim 1, and wherein:
said isolation member engages an inside surface of said housing.

8. The assembly of claim 1, and wherein:
said liquid passage is aligned along an axis substantially parallel with said aerosol conduit.

9. The assembly of claim 1, and wherein:
liquid flows thorough said liquid passage by gravity when said aerosol conduit is oriented in a substantially vertical direction.

10. The assembly of claim 1, and wherein:
said aerosol conduit includes an extension that extends further into said outlet chamber than said liquid reservoir, and wherein;
said shield portion accommodates said extension.

11. The assembly of claim 1, and wherein:
said shield portion is configured as a cap over an end of said aerosol conduit.

12. The assembly of claim 1, and wherein:
said aerosol vent is aligned along an axis substantially perpendicular to said aerosol conduit.

13. The assembly of claim 1, and wherein:
said aerosol vent is disposed radially away from an open end of said aerosol conduit.

14. An atomizing assembly with a liquid reservoir, which is refillable, for an electronic cigarette, comprising:
a housing;
a mouthpiece with an aerosol outlet formed therethrough, removably engaged with said housing;
a liquid reservoir disposed within said housing, and separated from said aerosol outlet by an outlet chamber, said liquid reservoir refillable by removing said mouthpiece and dispensing liquid into said outlet chamber;
an atomizing chamber, with an atomizer therein, adjacent to said liquid reservoir and opposite of said outlet chamber;
an aerosol conduit, which passes through said liquid reservoir, from said atomizing chamber to said outlet chamber, and which communicates an aerosol of liquid generated by said atomizer in response to a negative pressure induced at said mouthpiece;
an isolation member disposed within said outlet chamber and arranged to substantially seal said liquid reservoir from said outlet chamber;
a shield portion of said isolation member located about said aerosol conduit to prevent liquid from entering there into, and
a passage through said isolation member, which allows liquid within said outlet chamber to flow into said liquid reservoir, and enables the flow of said aerosol therethrough, and which is further oriented to prevent liquid from entering said aerosol conduit.

15. The assembly of claim 14, and wherein:
said housing is cylindrical and provides an outer enclosure of said liquid reservoir and said outlet chamber, and wherein
said mouthpiece is formed from a polymeric material that engages said housing.

16. The assembly of claim 14, and wherein:
liquid reservoir has an end open to said outlet chamber, thereby enabling liquid to enter.

17. The assembly of claim 16, and wherein:
said liquid reservoir is filled with an absorbent material to contain liquid.

18. The assembly of claim 14, and wherein:
said aerosol conduit is a tube, which defines an inner wall of said liquid reservoir.

19. The assembly of claim 14, and wherein:
said isolation member is formed from a resilient polymeric material.

20. The assembly of claim 14, and wherein:
said isolation member engages an inside surface of said housing.

21. The assembly of claim 14, and wherein:
said passage is aligned along an axis substantially parallel with said aerosol conduit.

22. The assembly of claim 14, and wherein:
liquid flows thorough said passage by gravity when said aerosol conduit is oriented in a substantially vertical direction.

23. The assembly of claim 14, and wherein:
said aerosol conduit includes an extension that extends further into said outlet chamber than said liquid reservoir, and wherein;
said shield portion accommodates said extension.

24. The assembly of claim 14, and wherein:
said shield portion is configured as a cap over an end of said aerosol conduit.

25. The assembly of claim 14, and wherein:
said passage comprise a vent portion, which is aligned along an axis substantially perpendicular to said aerosol conduit.

26. The assembly of claim 14, and wherein:
said passage is disposed radially away from an open end of said aerosol conduit.

* * * * *